United States Patent
Locke et al.

(10) Patent No.: US 10,086,117 B2
(45) Date of Patent: *Oct. 2, 2018

(54) WOUND CONNECTION PAD WITH RFID AND INTEGRATED STRAIN GAUGE PRESSURE SENSOR

(71) Applicant: KCI Licensing, Inc., San Antonio, TX (US)

(72) Inventors: Christopher Brian Locke, Bournemouth (GB); Richard Daniel John Coulthard, Verwood (GB); Juan L. Gonzalez, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 301 days.

This patent is subject to a terminal disclaimer.

(21) Appl. No.: 13/928,219

(22) Filed: Jun. 26, 2013

(65) Prior Publication Data

US 2014/0005618 A1 Jan. 2, 2014

Related U.S. Application Data

(60) Provisional application No. 61/665,755, filed on Jun. 28, 2012.

(51) Int. Cl.
*A61M 1/00* (2006.01)

(52) U.S. Cl.
CPC ........ *A61M 1/0031* (2013.01); *A61M 1/0025* (2014.02); *A61M 1/0088* (2013.01); *A61M 2205/3344* (2013.01); *A61M 2205/3592* (2013.01)

(58) Field of Classification Search
CPC ............................ A61M 1/00; A61M 1/0031
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

Ensminger, Dale, et al. Ultrasonics: Fundamentals, Technologies and Applications. 3rd Edition. CRC Press: Sep. 19, 2011. pp. 191-192. See attached.*

(Continued)

*Primary Examiner* — Benjamin Klein
*Assistant Examiner* — Sara Sass

(57) ABSTRACT

Systems, methods, and dressings are presented that involve using a RFID device in a dressing to provide pressure data or other data to a remote base unit. The dressing is an interactive dressing. The reduced pressure in the dressing may be monitored and used to control delivery of reduced pressure. In one instance, the pressure data at each dressing allows a plurality of tissue sites to be monitored and used with as single remote base unit. In another instance, devices and methods for assuring a proper pairing of reduced-pressure dressings and remote base units are also presented. Other systems, methods, and dressings are presented.

24 Claims, 9 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A * | 8/1996 | Gross .................. A61M 1/0088 604/313 |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,212,958 B1 * | 4/2001 | Conley ...................... 73/861.74 |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,661,335 B1 * | 12/2003 | Seal ........................ G01S 5/10 340/10.1 |
| 6,814,079 B2 | 11/2004 | Heaton et al. |
| 8,579,872 B2 * | 11/2013 | Coulthard et al. ............ 604/319 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0078366 A1 * | 4/2007 | Haggstrom et al. ............ 602/53 |
| 2010/0219942 A1 * | 9/2010 | Lee ........................ F01D 17/02 340/10.51 |
| 2011/0092927 A1 | 4/2011 | Wilkes et al. |
| 2012/0109083 A1 * | 5/2012 | Coulthard ............... A61F 13/02 604/319 |
| 2012/0242481 A1 * | 9/2012 | Gernandt ........... G06K 19/0705 340/539.13 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 102009039336 A1 | 3/2011 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | 2012/057881 A1 | 5/2012 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection,

(56) References Cited

OTHER PUBLICATIONS edited by V. Ye Volkov et al. (Chuvashia State University, Cheboksary, U.S.S.R. 1986);pp. 94-96.
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž Maksimović, Đ Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
International Search Report and Written Opinion for corresponding PCT/US2013/047943, dated Nov. 8, 2013.

\* cited by examiner

WOUND CONNECTION PAD WITH RFID AND INTEGRATED STRAIN GAUGE PRESSURE SENSOR

RELATED APPLICATION

The present invention claims the benefit, under 35 USC § 119(e), of the filing of U.S. Provisional Patent Application Ser. No. 61/665,755, entitled "WOUND CONNECTION PAD WITH RFID AND INTEGRATED STRAIN GAUGE PRESSURE SENSOR," filed 28 Jun. 2012, which is incorporated herein by reference for all purposes.

BACKGROUND

The present disclosure relates generally to medical treatment systems and, more particularly, but not by way of limitation, to interactive, wireless dressings, methods, and systems for use with reduced pressure.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to tissue through a porous pad or other manifold device. The porous pad distributes reduced pressure to the tissue and channels fluids that are drawn from the tissue. At times, a patient may have a large wound requiring treatment at numerous sites. Reduced pressure may also be used within a body cavity to remove fluids, among other things.

SUMMARY

According to an illustrative embodiment, a system for treating at least one tissue site with reduced pressure includes a first, wireless, reduced-pressure dressing for disposing proximate to the tissue site. The first, wireless, reduced-pressure dressing includes a distribution manifold, a sealing member or drape covering at least a portion of the distribution manifold, a Radio Frequency Identification (RFID) antenna, a first processor coupled to the RFID antenna, and a first sensor coupled to the first processor. The first sensor may be a pressure sensor comprising a strain gauge associated with a deflector, wherein the first sensor has a first side exposed to the ambient atmosphere and a second side exposed to the tissue site. The system also includes a remote base unit and a reduced-pressure source. The reduced-pressure source is fluidly coupled to the distribution manifold. The remote base unit includes a RFID antenna and a second processor.

According to another illustrative embodiment, a system for treating at least one tissue site with reduced pressure includes a first, wireless, reduced-pressure dressing for disposing proximate to the tissue site. The first, wireless, reduced-pressure dressing includes a sealing member or drape adapted to cover at least a portion of the tissue site, a first processor, a RFID antenna coupled to the first processor, and a first sensor coupled to the first processor. The first sensor may be a pressure sensor comprising a strain gauge associated with a deflector as described above.

According to another illustrative embodiment, a method for treating at least one tissue site with reduced pressure includes the steps of disposing a first, wireless, reduced-pressure dressing proximate to a first tissue site. The first, wireless, reduced-pressure dressing includes a distribution manifold adapted to be positioned adjacent to the tissue site for providing reduced pressure to the tissue site, a sealing member or drape covering at least a portion of the distribution manifold, a first processor, a RFID antenna coupled to the first processor, and a first sensor coupled to the first processor. The first sensor is a pressure sensor comprising a strain gauge and a deflector as described above. The method further includes providing a remote base unit that has a RFID reader, providing reduced pressure to the distribution manifold, transmitting a pressure inquiry signal from the RFID reader to the first, wireless, reduced-pressure dressing, and receiving a pressure message signal corresponding to the reduced pressure from the first, wireless, reduced-pressure dressing. The step of providing reduced pressure to the distribution manifold may exert a deflection force upon the first sensor that provides a deflection in the first sensor proportional to the reduced pressure. Thus, the pressure message signal may correspond to the deflection in the first sensor.

According to another illustrative embodiment, a method for treating at least one tissue site with reduced pressure includes the steps of disposing a first, wireless, reduced-pressure dressing proximate to a first tissue site. The first, wireless, reduced-pressure dressing includes a distribution manifold adapted to be positioned adjacent to the tissue site for providing reduced pressure to the tissue site, a sealing member or drape covering at least a portion of the distribution manifold, a first processor, a RFID antenna coupled to the first processor, and a first sensor coupled to the first processor. The first sensor may be a pressure sensor as described above. The method further includes providing a remote base unit having a RFID reader. The remote base unit also includes a second processor coupled to the RFID reader. The method further includes providing a reduced-pressure source; transmitting an ID inquiry signal from the remote base unit to the first, wireless, reduced-pressure dressing; receiving the ID inquiry signal at the first, wireless, reduced-pressure dressing and producing an ID message signal; transmitting the ID message signal from the first, wireless, reduced-pressure dressing to the remote base unit; receiving the ID message signal at the remote base unit; determining if the ID message signal is on an approved list; and activating the reduced-pressure source to provide reduced pressure to the distribution manifold if the ID message signal represents a dressing that is on the approved list or indicating an error if the ID message signal represents a dressing that is not on the approved list.

According to another illustrative embodiment, a system for treating at least one tissue site with reduced pressure includes a first, wireless, reduced-pressure dressing for disposing proximate to the tissue site. The first, wireless, reduced-pressure dressing includes a distribution manifold, a sealing member or drape covering at least a portion of the distribution manifold, a reduced-pressure interface for providing reduced pressure to the distribution manifold, a first RFID antenna, a first processor coupled to the first RFID antenna, a first sensor coupled to the first processor, and a membrane. The membrane covers at least a portion of the reduced-pressure interface and is initially in an occlusive state that prevents or hinders fluid flow through the reduced-pressure interface. The first, wireless, reduced-pressure dressing further includes a dissolution element proximate to the membrane that is adapted to change the membrane from the occlusive state to a non-occlusive state. When changed to the non-occlusive state, the membrane allows flow through reduced-pressure interface. The system further includes a remote base unit having a RFID reader and a second processor. The system also includes a reduced-pressure source fluidly coupled to the distribution manifold. The second processor is configured to transmit an activation signal with the RFID reader to the first, wireless, reduced-pressure dressing. In response to the activation signal, the first processor is configured to deliver power to the dissolution element to change the membrane from the occlusive state to the non-occlusive state. The second processor is configured to transmit an ID inquiry signal with the RFID reader to the first, wireless, reduced-pressure dressing. In response to the ID inquiry signal, the first processor is configured to transmit an ID message signal with the first RFID antenna. The second processor is adapted to receive the ID message signal via the RFID reader and to determine if the ID message signal represents an acceptable dressing.

According to another illustrative embodiment, a system for treating a tissue site with reduced pressure includes a wireless, reduced-pressure dressing that includes a distribution manifold, a sealing member or drape covering the distribution manifold, and a reduced-pressure interface. The system also includes a WISP device associated with the wireless, reduced-pressure dressing, a remote base unit comprising a RFID reader, and a reduced-pressure source fluidly coupled to the wireless, reduced-pressure dressing.

According to another illustrative embodiment, a method for treating at least one tissue site with reduced pressure includes disposing a first, wireless, reduced-pressure dressing proximate to a first tissue site. The first, wireless, reduced-pressure dressing includes a distribution manifold adapted to be positioned adjacent to the tissue site for providing reduced pressure to the tissue site, a sealing member or drape covering at least a portion of the distribution manifold, a reduced-pressure interface, and a membrane. The membrane is initially occlusive and covers at least a portion of the reduced-pressure interface. The membrane is adapted to prevent fluid flow through the reduced-pressure interface when in the occlusive state. The first, wireless, reduced-pressure dressing also includes a first processor, a RFID antenna coupled to the first processor, a first sensor coupled to the first processor, and a dissolution element proximate to the membrane that is operable, when activated, to change the membrane from an occlusive state to a non-occlusive state. The first sensor is a pressure sensor as described above. The dissolution element is coupled to the first processor. The method further includes providing a remote base unit having a RFID reader. The remote base unit includes a second processor. The method also includes providing a reduced-pressure source fluidly coupled to the reduced-pressure interface, transmitting an activation signal from the remote base unit to the first, wireless, reduced-pressure dressing, whereupon the first processor activates the dissolution element to change the membrane to the non-occlusive state, and providing reduced pressure from the reduced-pressure source to the reduced-pressure interface.

Other features and advantages of the illustrative embodiments will become apparent with reference to the drawings and detailed description that follow.

DETAILED DESCRIPTION OF ILLUSTRATIVE EMBODIMENTS

Figure 1A:
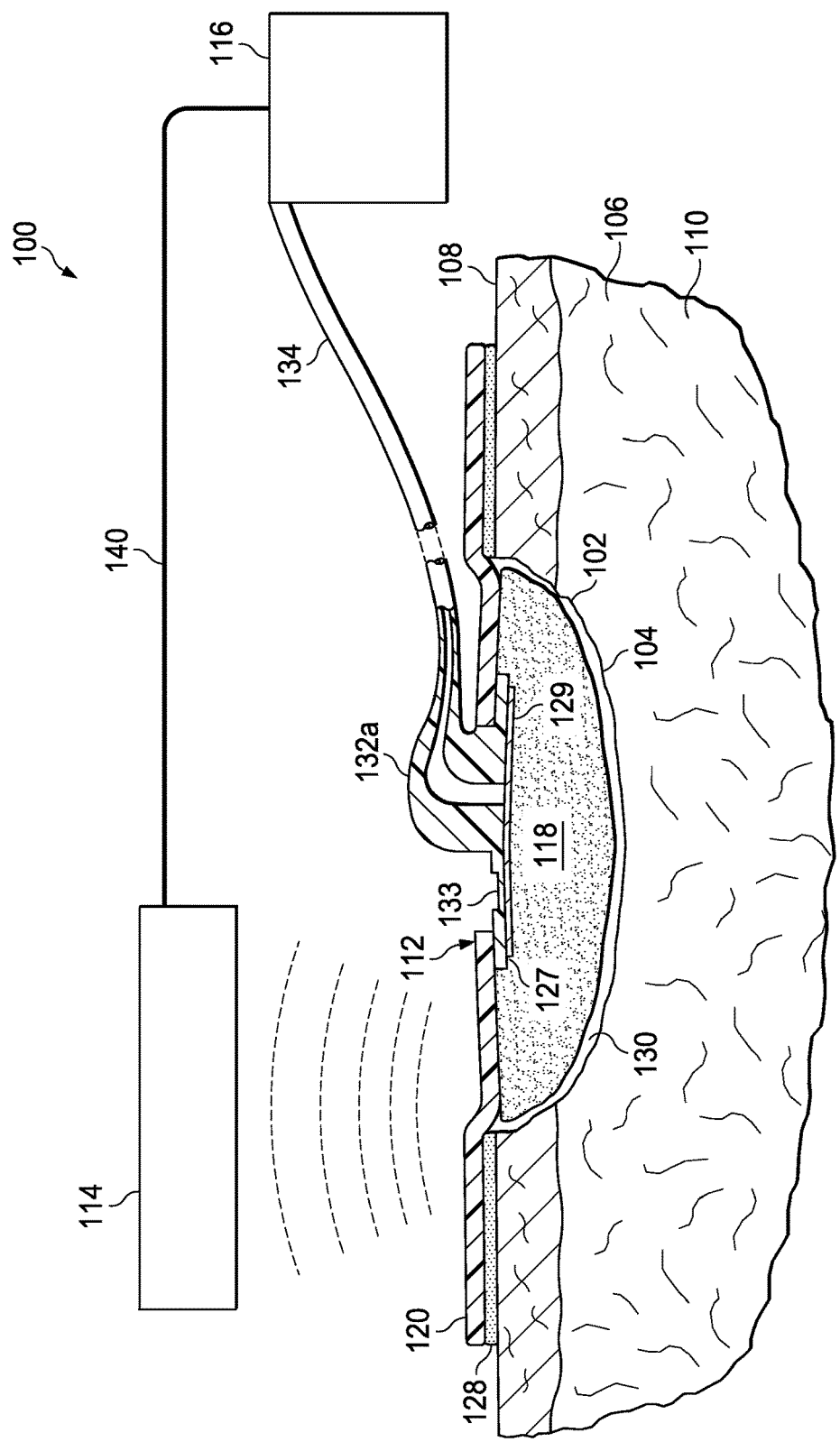
FIG. 1A is a schematic diagram, with a portion shown in cross section, of an illustrative embodiment of a system for treating at least one tissue site with reduced pressure.
Figure 1B:
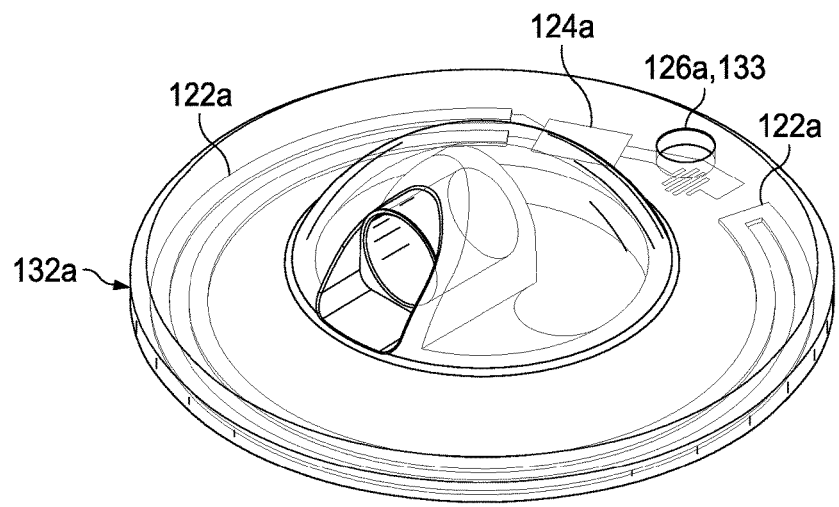
FIG. 1B is a schematic perspective view of an illustrative embodiment of a reduced pressure interface as depicted in FIG. 1A.
Figure 1C:
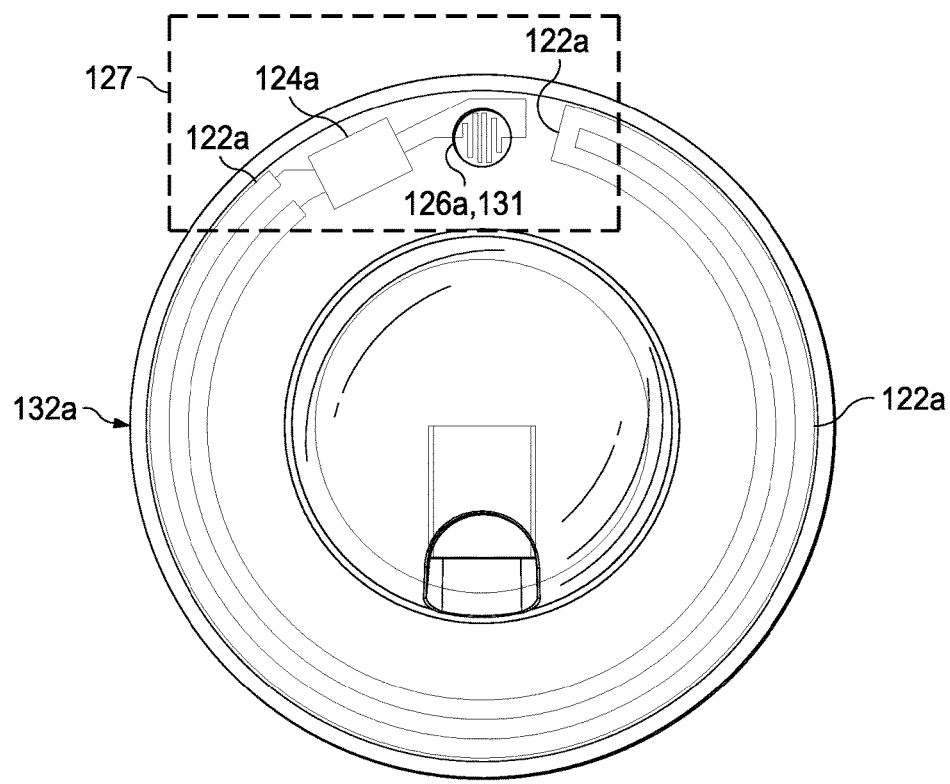
FIG. 1C is a bottom view of an illustrative embodiment of a reduced pressure interface as depicted in FIG. 1A.

In the following detailed description of the illustrative embodiments, reference is made to the accompanying drawings that form a part hereof. These illustrative embodiments are described in sufficient detail to enable those skilled in the art to practice the subject matter of this disclosure. Other embodiments may be utilized and logical, structural, mechanical, electrical, and chemical changes may be made without departing from the scope of this disclosure. To avoid detail not necessary to enable those skilled in the art to practice the embodiments described herein, the description may omit certain information known to those skilled in the art. The following detailed description is provided without limitation, and the scope of the illustrative embodiments are defined by the appended claims.

In treating a tissue site or sites on a patient with reduced pressure, it is typically desirable to maintain the reduced pressure in a therapeutic range. While the amount and nature of reduced pressure applied to a tissue site will typically vary according to the application, the reduced pressure will typically be between −5 mm Hg and −500 mm Hg, and more typically between −75 mm Hg and −300 mm Hg, and even more typically between −100 to −200 mm Hg. In some instances, failure to provide reduced pressure to a tissue site can lead to complications. Accordingly, it may be desirable to monitor the pressure at each tissue site undergoing treatment.

To accommodate multiple tissue sites, e.g., multiple wounds, multiple conduits may be used to deliver reduced pressure. For example, a single reduced-pressure source may be used with the multiple conduits branched off of one conduit to provide reduced pressure to multiple tissue sites. Currently, pressure monitoring is typically located in existing reduced-pressure sources, and only one conduit communicates pressure from the reduced-pressure source. If only one conduit associated with one tissue site is monitored, as is the case when monitoring is done at the reduced-pressure source alone, pressures at other tissue sites are unmonitored. With at least some of the illustrative embodiments herein, each tissue site of the plurality of tissue sites is monitored so that any disruption with reduced pressure delivery may be identified and addressed. Moreover, other parameters may be monitored to track progress or identify issues with healing of the tissue sites.

Reduced pressure may be used to treat open wounds and to promote the granulation of tissue. Reduced pressure may also be applied to a tissue site internal to a patient to remove fluids. For example, reduced pressure may be used to remove ascites from a patient's abdomen. In such situations it may be desirable to know the pressure at the internal location as well as other parameters. Reduced pressure may also be used for other applications to promote healing. The illustrative embodiments herein may be operable to perform these tasks.

The illustrative embodiments herein involve using Radio Frequency Identification (RFID) technology, including enhanced RFID technology, to wirelessly transmit and receive sensing information from a reduced-pressure dressing. RFID uses a RFID tag or label that is on a target and a RFID reader that energizes and reads a signal from the RFID tag. Most RFID tags include an integrated circuit for storing and processing information, a modulator, and demodulator. To enhance the RFID tag, a microcontroller (or processor) and sensor are incorporated that allow sensing and optional computational functions to occur. RFID tags can be passive tags, active RFID tags, and battery-assisted passive tags. Generally, passive tags use no battery and do not transmit information unless they are energized by a RFID reader. Active tags have an on-board battery and can transmit autonomously, i.e., without being energized by a RFID reader. Battery-assisted passive tags typically have a small battery on-board that is activated in the presence of a RFID reader.

In one illustrative embodiment, the enhanced RFID technology is a Wireless Identification and Sensing Platform (WISP) device. WISPs involve powering and reading a WISP device, analogous to a RFID tag (or label), with a RFID reader. The WISP device harvests the power from the RFID reader's emitted radio signals, performs sensing functions, and optionally performs computational functions. The WISP device transmits a radio signal with information to the RFID reader. The WISP device has a tag or antenna that harvests energy and a microcontroller, or processor, that can perform a variety of tasks, such as sampling sensors. The WISP device reports data to the RFID reader. In one illustrative embodiment, the WISP device includes an integrated circuit with power harvesting circuitry, demodulator, modulator, microcontroller, sensors, and may include one or more capacitors for storing energy.

Figure 2A:
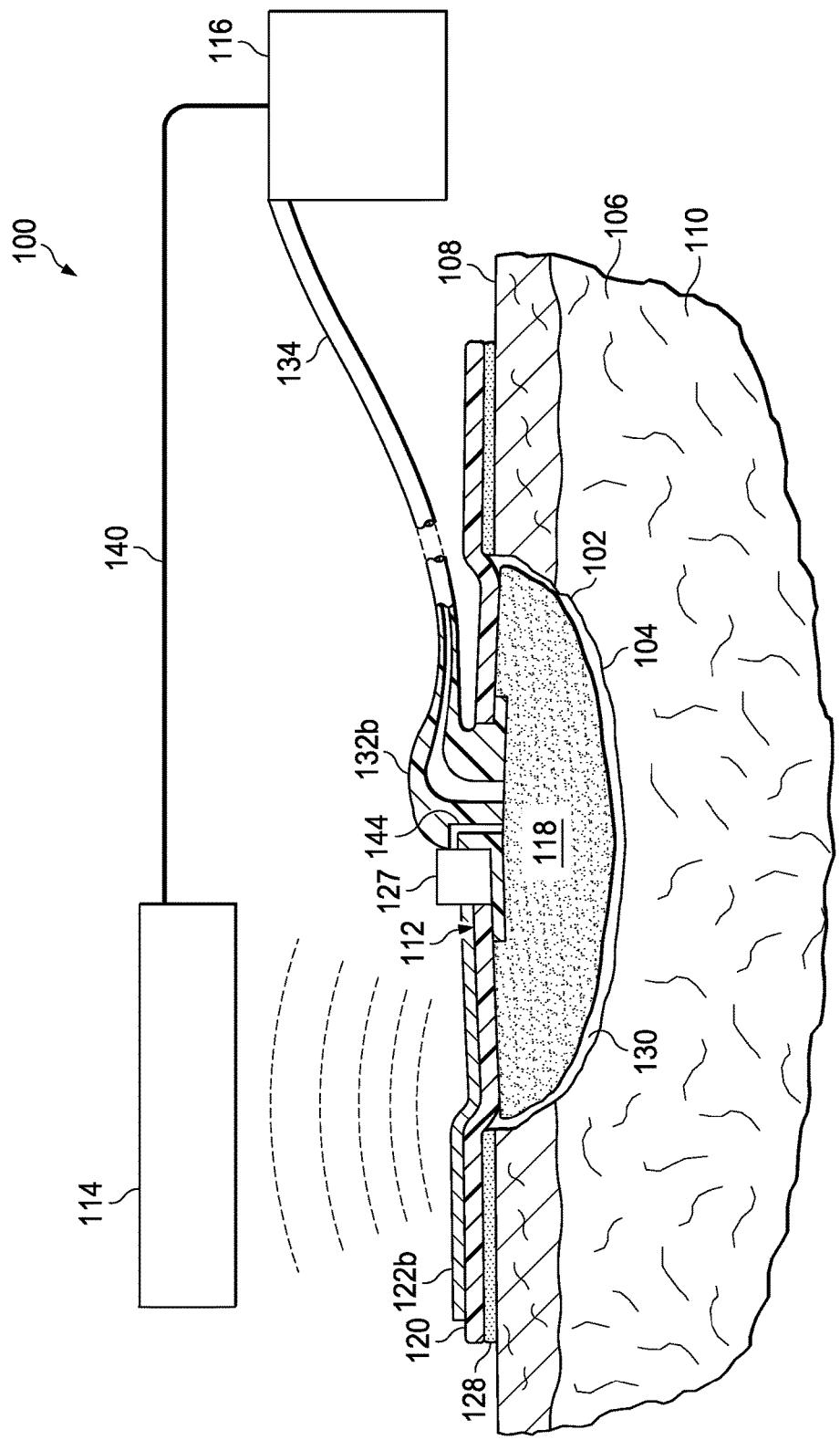
FIG. 2A is a schematic diagram, with a portion shown in cross section, of another embodiment of a system for treating at least one tissue site with reduced pressure.
Figure 2B:
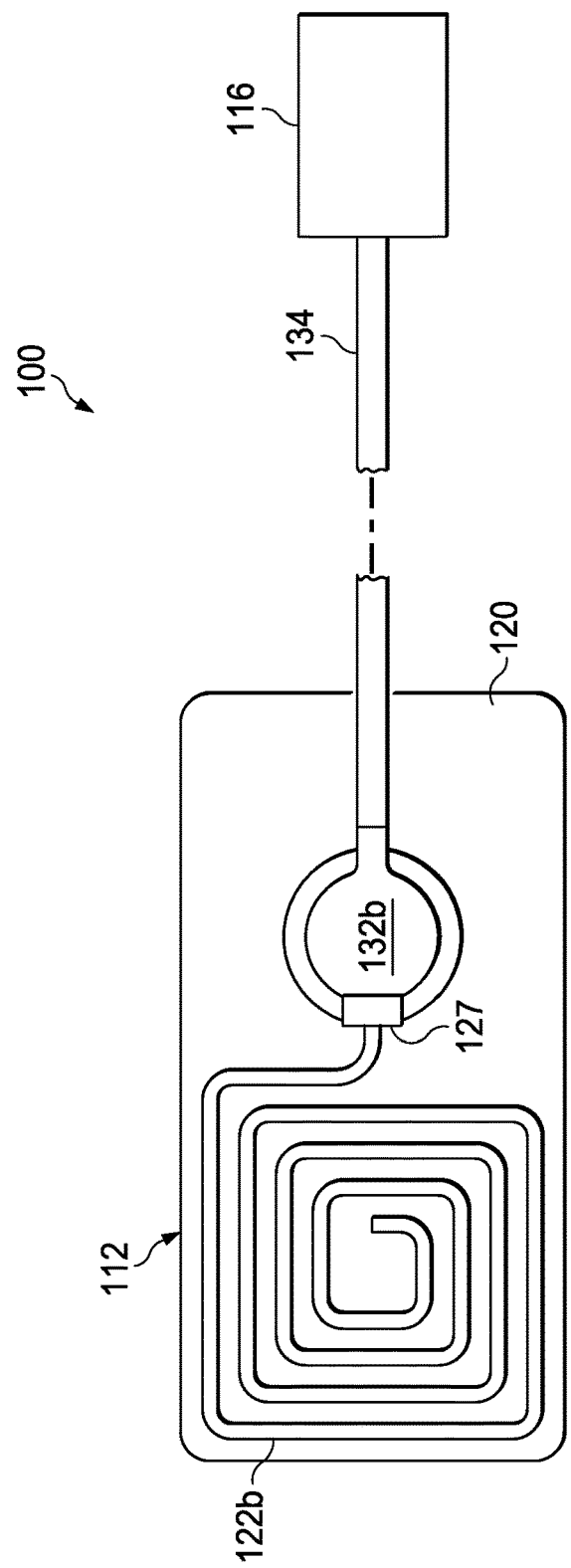
FIG. 2B is a schematic top view of the first, wireless, reduced-pressure dressing of the system of FIG. 2A.
Figure 3:
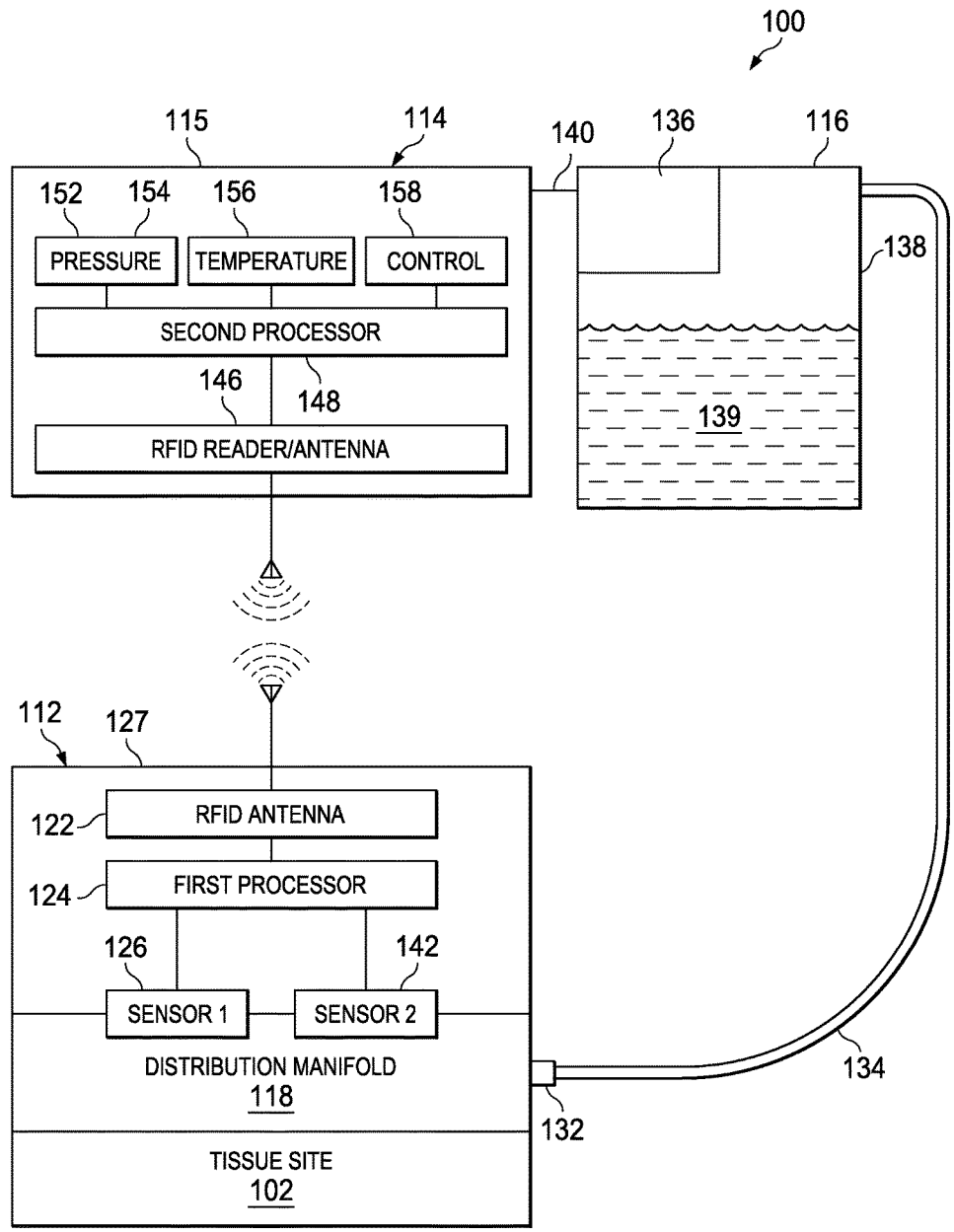
FIG. 3 is a schematic diagram, with a portion shown in cross section, of an illustrative embodiment of a system for treating at least one tissue site with reduced pressure.

Referring now to the drawings and initially to FIGS. 1-3, a system 100 for treating at least one tissue site 102, e.g., a wound site 104, with reduced pressure is presented. The illustrative wound site 104 is shown through epidermis 108 and into the subcutaneous tissue 110 of a patient 106. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 102 may include removal of fluids, e.g., exudate or ascites.

The system 100 may be used to treat the tissue site 102 with reduced pressure to help form granulation tissue (reduced pressure therapy), to remove fluids without promoting tissue growth, or any other purpose for which reduced pressure is helpful. The system 100 includes a first, wireless, reduced-pressure dressing 112 for disposing proximate to the tissue site 102, a remote base unit 114, and a reduced-pressure source 116.

The first, wireless, reduced-pressure dressing 112 may include a distribution manifold 118, a sealing member 120 (or drape) covering at least a portion of the distribution manifold 118, a first RFID antenna 122, a first processor 124 coupled to the first RFID antenna 122, and a first sensor 126 coupled to the first processor 124. The first processor 124 and first sensor 126 may be associated with a board 127 or housing. In one embodiment discussed below, the board 127 may be a flexible printed circuit comprising the first RFID antenna 122, the first processor 124, and the first sensor 126.

The sealing member 120 creates a fluid seal over the distribution manifold 118 on a portion of a patient's epidermis 108, and may help provide a fluid seal at other locations. "Fluid seal," or "seal," may be a seal adequate to maintain reduced pressure at a desired tissue site given the particular reduced-pressure source or subsystem involved. The sealing member 120 may include an attachment device 128. The sealing member 120 creates a sealed space 130 in which the distribution manifold 118 may be positioned. A reduced-pressure interface 132, or connection pad, may be placed through an aperture in the sealing member 120 to provide reduced pressure into the sealed space 130 and in particular to the distribution manifold 118. Other wireless reduced-pressure dressings may be used as part of the system 100 to accommodate multiple tissue sites, and the additional wireless reduced-pressure dressings may be analogous to the first, wireless, reduced-pressure dressing 112.

With respect to the distribution manifold 118, the term "manifold" as used herein generally refers to a substance or structure that is provided to assist in applying reduced pressure to, delivering fluids to, or removing fluids from a tissue site, e.g., tissue site 102. The distribution manifold 118 typically includes a plurality of flow channels or pathways that distribute fluids provided to and removed from the tissue site 102 around the distribution manifold 118. In one illustrative embodiment, the flow channels or pathways are interconnected to improve distribution of fluids provided or removed from the tissue site 102. The distribution manifold 118 may also be a biocompatible material that is capable of being placed in contact with the tissue site 102 and distributing reduced pressure to the tissue site 102. Examples of manifolds 118 may include, without limitation, devices that have structural elements arranged to form flow channels, such as, for example, cellular foam, open-cell foam, porous tissue collections, liquids, gels, and foams that include, or cure to include, flow channels. The examples are not mutually exclusive.

The distribution manifold 118 may be porous and may be made from foam, gauze, felted mat, or any other material suited to a particular biological application. In one embodiment, the distribution manifold 118 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include "closed cells." In some situations, the distribution manifold 118 may also be used to distribute fluids such as medications, antibacterials, growth factors, and various solutions to the tissue site 102. Other layers may be included in or on the distribution manifold 118 such as absorptive materials, wicking materials, hydrophobic materials, and hydrophilic materials.

In one illustrative embodiment, the distribution manifold 118, or portions of the distribution manifold 118, may be constructed from bioresorbable materials that may remain in a patient's body following use of the first, wireless, reduced-pressure dressing 112. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 118 may further serve as a scaffold for new cell growth, or a scaffold material may be used in conjunction with the distribution manifold 118 to promote cell growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 120 may be any material that provides a fluid seal. The sealing member 120 may, for example, be an impermeable or semi-permeable, elastomeric material. "Elastomeric" means having the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional examples of sealing member materials include a silicone drape, 3M Tegaderm® drape, and a polyurethane (PU) drape, such as one available from Avery Dennison Corporation of Pasadena, Calif.

The attachment device 128 may be used to maintain the sealing member 120 against the patient's epidermis 108, or another layer, such as a gasket or additional sealing member. The attachment device 128 may take numerous forms. For example, the attachment device 128 may be a medically acceptable, pressure-sensitive adhesive that extends about a periphery, a portion, or the entire sealing member 120.

The first, wireless, reduced-pressure dressing 112 provides reduced pressure to one or more tissue sites 102. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the distribution manifold 118 and proximate the tissue site 102. As the hydrostatic pressure around the tissue site 102 approaches the desired reduced pressure, the flow may subside, and the reduced pressure may be maintained. Unless otherwise indicated, values of pressure stated herein are gauge pressures. Absolute pressure is referenced at times. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure refers to a relative reduction in absolute pressure.

The reduced-pressure interface 132 may be a structure for fluidly coupling a reduced-pressure delivery conduit 134 to the distribution manifold 118. The reduced-pressure interface 132 may be a molded structure, a medical conduit, e.g., a portion of reduced-pressure delivery conduit 134, applied to the distribution manifold 118, or similar device. As discussed below in connection with FIG. 4, a membrane, when in an occlusive state, may prevent or hinder flow of fluid through the reduced-pressure interface 132.

The reduced-pressure source 116 provides reduced pressure. The reduced-pressure source 116 may be any device or source for supplying a reduced pressure, such as a vacuum pump 136, wall suction, micro-pump, or other source. As a component of the reduced-pressure source 116, or as a separate member, a canister 138 may be included to receive and retain fluids 139. The remote base unit 114 may be electrically coupled by coupling 140, e.g., a wire or wireless signal, to the reduced-pressure source 116 to provide a pressure control signal to control the delivery of reduced pressure to the first, wireless, reduced-pressure dressing 112 as will be discussed further below. The reduced-pressure source 116 and the remote base unit 114 may be an integrated unit in some embodiments. "Remote" as used in the context of "remote base unit" typically means displaced from a wireless, reduced-pressure dressing by a distance greater than several millimeters and may include a base unit immediately adjacent to a wireless, reduced-pressure dressing but not electrically coupled.

The first sensor 126 may be, for example, a pressure sensor, temperature sensor, pH sensor, humidity sensor, Volatile Organic Compounds (VOC) sensor, blood sensor, or growth factors sensor. The first processor 124 may be coupled to, or in communication with, the first sensor 126 and the first RFID antenna 122.

In one embodiment, the first sensor 126 may be a pressure sensor. The first sensor 126 may thus develop a signal indicative of pressure sensed at a desired site in or on the first, wireless, reduced-pressure dressing 112 and that signal may be referred to as a pressure message signal.

Referring to the embodiment of FIGS. 1A-1D, the first sensor 126 may be a first sensor 126a, namely a pressure sensor comprised of a strain gauge 131 associated with a deflector 133. The strain gauge 131 may be a component printed on the board 127 and positioned in a layered relationship with the deflector 133 as described below.

As shown in FIGS. 1A-1D, the board 127 may be a flexible printed circuit comprising a first processor 124a analogous to the first processor 124, the strain gauge 131, and a first RFID antenna 122a analogous to the first RFID antenna 122. The first processor 124a may be in communication with the strain gauge 131 and the first RFID antenna 122a on the board 127. However, the first RFID antenna 122a and the first processor 124a may also be separate components in communication with the strain gauge 131. The flexible printed circuit may comprise a flexible polymer film that provides a foundation layer. The polymer may be a polyester (PET), polyimide (PI), polyethylene napthalate (PEN), polyetherimide (PEI), or a material with similar mechanical and electrical properties. The flexible circuit may include one or more laminate layers formed of a bonding adhesive. In addition, a metal foil, such as a copper foil, may be used to provide one or more conductive layers to the flexible printed circuit material. Generally, the conductive layer is used to form circuit elements that may be etched into the conductive layer. The conductive layer may be applied to the foundation layer by rolling (with or without adhesive) or by electro-deposition.

Continuing with FIGS. 1A-1D, the board 127 may be formed integrally with a reduced-pressure interface 132a, or connection pad, that is analogous to the reduced-pressure interface 132. For example, the board 127 may be bonded or insert-molded in the reduced-pressure interface 132a. The board 127 may also be printed on the reduced-pressure interface 132a subsequent to the manufacture of the reduced-pressure interface 132a. Although FIGS. 1A-1D depict the board 127 positioned on a side of the reduced-pressure interface 132a facing the tissue site 102, any suitable surface on the reduced-pressure interface 132a may be used. Further, the board 127 may be associated with other components of the first, wireless, reduced pressure dressing 112 in the manner described herein.

As shown in FIGS. 1A-1D, the positioning of the deflector 133 is on the reduced-pressure interface 132a. The board 127 may be associated with the reduced-pressure interface 132a as described above such that the deflector 133 is aligned in a layered relationship with the strain gauge 131. The deflector 133 may be any deformable substrate having predictable deformation characteristics and capable of supporting the strain gauge 131. The deflector 133 may be molded or otherwise formed as a part of the reduced pressure interface 132a. In one embodiment, the deflector 133 may be formed as part of the board 127 described above.

The first sensor 126a provides a fluid barrier to the tissue site 102, having a first side exposed to the ambient atmosphere and a second side exposed to the tissue site 102. A coating 129 may be used to electrically isolate the first sensor 126a from the tissue site 102 and/or the ambient atmosphere.

Figure 1D:
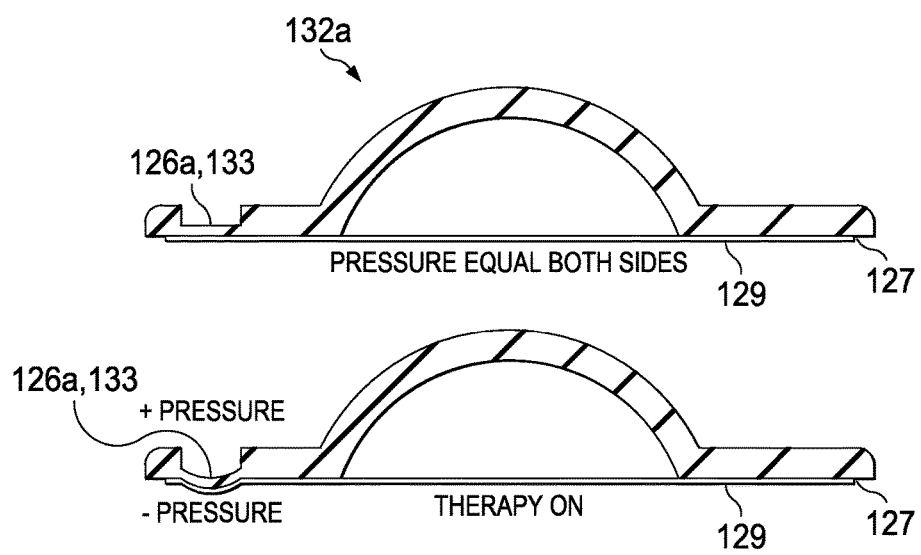
FIG. 1D is a schematic cross section view of a reduced pressure interface as depicted in FIG. 1, illustrating deformation of a first sensor due to the application of reduced pressure during treatment.

As shown in FIG. 1D, use of the flexible circuit as board 127 in combination with the deflector 133 permits the first sensor 126a to deflect when subjected to a pressure differential between the ambient atmosphere and the tissue site 102. Specifically, the strain gauge 131 and the deflector 133 comprising the first sensor 126a may be associated with one another or otherwise configured such that a deflection of the deflector 133 imparts a corresponding deflection of the strain gauge 131. Reduced pressure delivered to the tissue site 102 during therapy may exert a deflection force upon the first sensor 126a, causing the first sensor 126a to deflect or otherwise deform. As shown in FIG. 1D, when reduced pressure therapy is on, the first sensor 126a may deflect toward a negative pressure differential at the tissue site, depicted as "−PRESSURE", and away from the ambient atmosphere, depicted as "+PRESSURE." Such a deflection of the first sensor 126a may change an electrical resistance value of the strain gauge 131, and result in a pressure message signal being sent to the first processor 124a. The pressure message signal indicates the reduced pressure status of the tissue site 102. The thickness and material properties of the board 127 and the deflector 133 may be varied to adjust the pressure sensitivity of the first sensor 126a. Further, including lamina having varying elasticity in the deflector 133 and/or the board 127 may also provide adjustment for the pressure sensitivity of the first sensor 126a. In one embodiment, the deflection of the strain gauge 131 is proportional to a change in the electrical resistance value of the strain gauge 131.

Other embodiments for the strain gauge 131 can include a pressure switch (not shown) printed on a flexible circuit and associated with the deflector 133 as described above. In this embodiment, the flexible circuit and deflector 133 may be designed to deflect in a non-linear manner with maximum deflection occurring when a threshold pressure is reached. This configuration may indicate whether a pressure is above or below a particular level. Multiple pressure switches with different deflection force points may be combined to provide a high, medium, and low output configuration.

Referring to an another embodiment in FIGS. 2A-2B, provided is a reduced-pressure interface 132b that is analogous to the reduced-pressure interface 132. The reduced-pressure interface 132b comprises one or more pressure conduits or channels 144 in fluid communication with the board 127 to provide reduced pressure for sampling purposes. In this embodiment, the board 127 may comprise a first processor 124b analogous to the first processor 124, and a first sensor 126b analogous to the first sensor 126. The first processor 124b may be in communication with the first sensor 126b and a first RFID antenna 122b, the first RFID antenna 122b being analogous to the first RFID antenna 122. The sensor 126b receives a pressure input from the channel 144, which results in a pressure message signal being sent to the first processor 124b.

Continuing with FIGS. 1-3, a second sensor 142 may also be included and coupled to the first processor 124. The second sensor 142 may be any type of sensor such as those previously mentioned for the first sensor 126. It will be appreciated that the first RFID antenna 122, the first processor 124, and the first sensor 126 may comprise a Wireless Identification and Sensing Platform (WISP) device. In one embodiment, the second sensor 142 is a temperature sensor, such as, without limitation, a temperature sensing diode or a thermistor. Use of a temperature sensor for the second sensor 142 may enhance the accuracy of the pressure measurements described herein. While two sensors 126, 142 have been described, additional sensors may be provided if desired.

The first sensor 126, the second sensor 142, or any other sensors may be located at any location in the first, wireless, reduced-pressure dressing 112. In one illustrative embodiment, the first sensor 126 may be adjacent to the distribution manifold 118. In another illustrative embodiment, the first sensor 126 may be at a remote portion of the sealing member 120. In yet another illustrative embodiment, the sensors, e.g., the first sensor 126, may be laminated to the sealing member 120 or otherwise attached to a portion of the sealing member 120 and may sample pressure in the sealed space 130.

In one illustrative embodiment, a battery is not associated with the first, wireless, reduced-pressure dressing 112. In other words, the first, wireless, reduced-pressure dressing 112 is passive. In such an embodiment, all the necessary energy for the first processor 124 and first sensor 126 (and any additional, optional sensors, e.g., second sensor 142) is harvested from signals received by the first RFID antenna 122 from the remote base unit 114. In other embodiments, a battery may be included to provide the necessary power. With the power from the battery, the first, wireless, reduced-pressure dressing 112 may transmit signals independent of any signal from the remote base unit 114. In another illustrative embodiment, a battery may be included to provide a portion of the necessary power.

The remote base unit 114 may include a board or similar structure 115 that includes an RFID reader 146 and a second processor 148. The remote base unit 114 may also include a first display 152, e.g., a pressure indicator 154. The first display 152 or pressure indicator 154 may display a quantity measured by the first sensor 126 or an indication of adequate pressure. Similarly, additional displays or indicators may be included, e.g., a temperature display 156. One display may be used for displaying multiple items, e.g., the data from multiple sensors. A control panel 158, such as a push-button panel or graphical user interface, may be included to receive input from a user. The second processor 148 may be connected by coupling 140 to the reduced-pressure source 116 to provide a control signal. The control signal allows for automated adjustments to the pressure at the tissue site 102 by controlling the pressure supplied by the reduced-pressure source 116.

The RFID reader 146 may be a transceiver for transmitting to and receiving signals from the first RFID antenna 122. If not already converted, the RFID reader 146 may convert received signals to digital format and provide the signals to the second processor 148. The remote base unit 114 may read signals as close as several millimeters away or as far as 30 feet or more away or any distance between, e.g., 5, 10, or 20 feet. The remote base unit 114 may poll as often as desired, e.g., every ½ second, every second, every hour, or any other time interval.

The second processor 148 includes memory and instructions necessary to perform various desired steps. For example, a pairing protocol may be executed. In the pairing protocol, the second processor 148 with the RFID reader 146 transmits an ID inquiry signal to the first, wireless, reduced-pressure dressing 112 to inquire about the identification of the first, wireless, reduced-pressure dressing 112. In response, the first processor 124 transmits an ID message signal. If the first, wireless, reduced-pressure dressing 112 is not suitable for use with the remote base unit 114 as determined by comparing the ID message with an approved list or by information contained in the ID message signal itself, the remote base unit 114 will not proceed with executing instructions as part of therapy. This protocol should safeguard against using a dressing that is not approved and which may underperform with the remote base unit 114.

As an illustrative example, the second processor 148, the RFID reader 146, the first RFID antenna 122, and the first processor 124 may be configured to perform the following steps: transmitting an ID inquiry signal from the remote base unit 114 to the first, wireless, reduced-pressure dressing 112; receiving the ID inquiry signal at the first, wireless, reduced-pressure dressing 112 and producing an ID message signal; transmitting the ID message signal from the first, wireless, reduced-pressure dressing 112 to the remote base unit 114; receiving the ID message signal at the remote base unit 114; determining if the ID message signal represents a dressing on an approved list; and activating the reduced-pressure source 116 to provide reduced pressure to the distribution manifold 118 if the ID message signal represents a dressing that is on the approved list (or otherwise acceptable) or indicating an error if the ID message signal represents a dressing that is not on the approved list.

Figure 4:
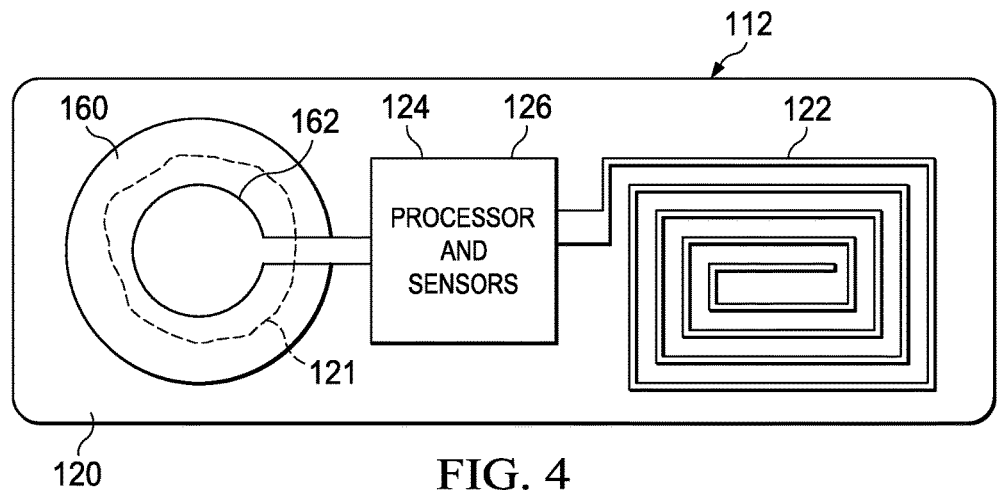
FIG. 4 is a schematic top view of an illustrative embodiment of a first, wireless, reduced-pressure dressing.

Referring now primarily to FIG. 4, another illustrative embodiment of a first, wireless, reduced-pressure dressing 112 is presented. The first, wireless, reduced-pressure dressing 112 of FIG. 4 is similar to the first, wireless, reduced-pressure dressing 112 of FIGS. 1-3. A sealing member 120, or film, covers the first RFID antenna 122, the first processor 124, and the first sensor 126. In this embodiment, a reduced-pressure interface (not shown but analogous to the reduced-pressure interface 132a/b of FIGS. 1-3) may be coupled over an aperture 121 in the sealing member 120 to allow fluid communication, but initially a membrane 160 prevents or hinders flow through the aperture 121.

The membrane 160 may have an occlusive state and a non-occlusive state. The membrane 160 may be in the occlusive state when the membrane 160 is an integral layer and may be non-occlusive when one or more apertures are created in the membrane 160 that allow fluid flow through the membrane. When initially over aperture 121 in the occlusive state, flow through the aperture 121 is substantially prevented or hindered, but when the membrane 160 is changed to the non-occlusive state, flow through the membrane 160, and thus, through the aperture 121 may occur. The membrane 160 may move from the occlusive state to the non-occlusive state in response to an activating event, e.g., the application of heat, light, ultrasound, a chemical, or other activating agent. For example, in one illustrative embodiment, a dissolution element 162 is disposed proximate to the membrane 160 and is adapted or otherwise operable to change the membrane 160 from an occlusive state to a non-occlusive state. The dissolution element 162 may be activated by the first processor 124 to produce the activating event. In other embodiments, the dissolution element 162 may be activated by the second processor 148 or an external stimulus.

The dissolution element 162 may be, for example and not by way of limitation, an electrically resistive heating element. Power may be supplied from the first processor 124 to the dissolution element 162 to sufficiently activate the electrically resistive heating element to melt, dissolve, or otherwise create an aperture in the membrane 160. In another illustrative embodiment, the dissolution element 162 may be an ultrasonic device that creates an aperture in membrane 160 when activated. In another illustrative embodiment, the dissolution element 162 may be a chemical distribution device that upon receiving a signal from the first processor 124 releases an agent that causes the membrane 160 to dissolve, at least in part, to create an aperture 121. In still another illustrative embodiment, the dissolution element 162 may be a light with a first wavelength and the membrane 160 reacts to the light with the first wavelength and dissolves at least a portion to create an aperture.

The membrane 160 may be made from numerous materials depending on the activation device used as the dissolution element 162. For example, the membrane 160 may comprise a semi-crystalline thermoplastic film, such as LDPE, HDPE, PP, PA, having a thickness in the range 15 μm-100 μm. The exact thickness of the membrane 160 depends on the material selected and the level of reduced pressure that the membrane 160 will be required to resist. The temperature required to rupture the membrane 160 should be approaching or at the melting point of the polymer chosen. If heated while the membrane 160 is under strain from applied reduced pressure, the temperature required to breakdown or dissolve the membrane 160 may be reduced.

The dissolution element 162 may be a component laminated to the membrane 160 during the manufacture of the membrane 160 or attached later in production. The dissolution element 162 may be a conductive component that is molded into the membrane 160 or added to the membrane 160 so that the membrane 160 itself is conductive. The conductive material may be metallic or one of the other materials that are commonly used to provide conductivity to polymers. Although the temperature required to melt some of the membrane or film materials mentioned may be greater than 100° C., the dissolution element 162 is separated from the patient sufficiently to avoid injury or other potential complications. Moreover, the membrane 160 may be extremely thin such that very little energy is required to form an aperture through the membrane 160.

Referring now primarily to FIGS. 1-4, if the first, wireless, reduced-pressure dressing 112 includes the membrane 160 and dissolution element 162, an initial activation may be carried out by the remote base unit 114 and first processor 124. As an illustrative example, the remote base unit 114 may transmit an activation signal from the remote base unit 114 to the first, wireless, reduced-pressure dressing 112. Upon receiving the activation signal, the first processor 124 activates the dissolution element 162 to change the membrane 160 to the non-occlusive state such as by creating an opening over the aperture 121. Reduced pressure from the reduced-pressure source 116 may then be delivered through the reduced-pressure interface 132 and the aperture 121 to the distribution manifold 118. If a user is attempting to use a remote base unit that is not designed for use with the first, wireless, reduced-pressure dressing 112, the remote base unit will not respond to the activation signal and will not change the membrane 160 from the occlusive state to the non-occlusive state. Accordingly, the first, wireless, reduced-pressure dressing 112 would be unable to establish fluid flow through the membrane 160 to the distribution manifold 118.

According to one illustrative embodiment, in operation, the first, wireless, reduced-pressure dressing 112 is disposed proximate to the tissue site 102. The distribution manifold 118 is placed adjacent to the tissue site 102. The sealing member 120 is releaseably attached to the epidermis 108 with the attachment device 128. The reduced-pressure delivery conduit 134 is fluidly coupled between the reduced-pressure interface 132 and the reduced-pressure source 116. The remote base unit 114 may be activated by the user with the control panel 158.

The remote base unit 114 may initially transmit an activation signal to the first, wireless, reduced-pressure dressing 112 to cause the membrane 160 to change from an occlusive state to a non-occlusive state as previously described. The remote base unit 114 may then transmit an ID inquiry signal to identify the dressing type. The first, wireless, reduced-pressure dressing 112 receives the ID inquiry signal and, in response, transmits an ID message signal indicative of the dressing type. The second processor 148 may receive the ID message signal and look up the ID message signal or otherwise determine if the dressing represented by the ID message signal is acceptable. If the dressing is acceptable, the second processor 148 may cause a control signal to be sent, e.g., by coupling 140, to the reduced-pressure source 116 to activate the reduced-pressure source 116 and begin treatment with reduced pressure. As part of the activation process, the first, wireless, reduced pressure dressing 112 may be permanently altered to indicate a used state, e.g., by storing a code or burning circuit trace, thereby preventing a potentially unsanitary reuse of the first, wireless, reduced pressure dressing 112. In another embodiment, the dressing type may be validated before an activation signal is sent.

The remote base unit 114 may be configured to transmit a pressure inquiry signal to the first, wireless, reduced-pressure dressing 112. In response, the first, wireless, reduced-pressure dressing 112 ascertains the pressure with the first sensor 126 and transmits a pressure message signal to the remote base unit 114. Based on the pressure message signal, the remote base unit 114 determines if the pressure is greater than a first target pressure (on an absolute scale), and if so, continues operation of the reduced-pressure source 116. If the pressure message signal indicates that the pressure is less than the first target pressure (on absolute scale), the second processor 148 may send a control signal to the reduced-pressure source 116 to decrease or stop the delivery of reduced pressure. Operation of the reduced-pressure source 116 may be by manipulation of a valve or power to a vacuum pump or other like techniques. The remote base unit 114 may interrogate the first, wireless, reduced-pressure dressing 112 from time to time to monitor the pressure. If the pressure becomes greater than the first target pressure (on an absolute scale), the reduced-pressure source 116 will again be activated by a control signal. Thus, a feedback loop may be utilized. If a loss of communication occurs, such as between the remote base unit 114 and the first, wireless, reduced-pressure dressing 112, an error signal may be generated to alert the user.

If a patient has a plurality of tissue sites 102 requiring treatment, a plurality of the wireless, reduced-pressure dressings 112 may be used. For example, the first, wireless, reduced-pressure dressing 112 may be placed at the first tissue site 102 and a second, wireless, reduced-pressure dressing (not shown, but analogous to the reduced-pressure dressing 112) may be placed at a second tissue site. Because the signals include unique identification information, the remote base unit 114 may communicate with both the first, wireless, reduced-pressure dressing 112 and the second, wireless, reduced-pressure dressing. This arrangement allows monitoring and control of reduced pressure at each of the plurality of tissue sites. Multiple remote base units 114 and multiple reduced pressure sources 116 may also be used. For example, each first processor 124 may include dynamic RAM that includes a register that is configured when paired to a particular remote base unit 114. Thus, the first, wireless, reduced-pressure dressing 112 is able to distinguish which remote base unit 114 has been assigned. The first, wireless, reduced-pressure dressing 112 may include a reset button that transmits a reset signal to the first processor 124 to allow the dressing and base association to be changed.

Figure 5:
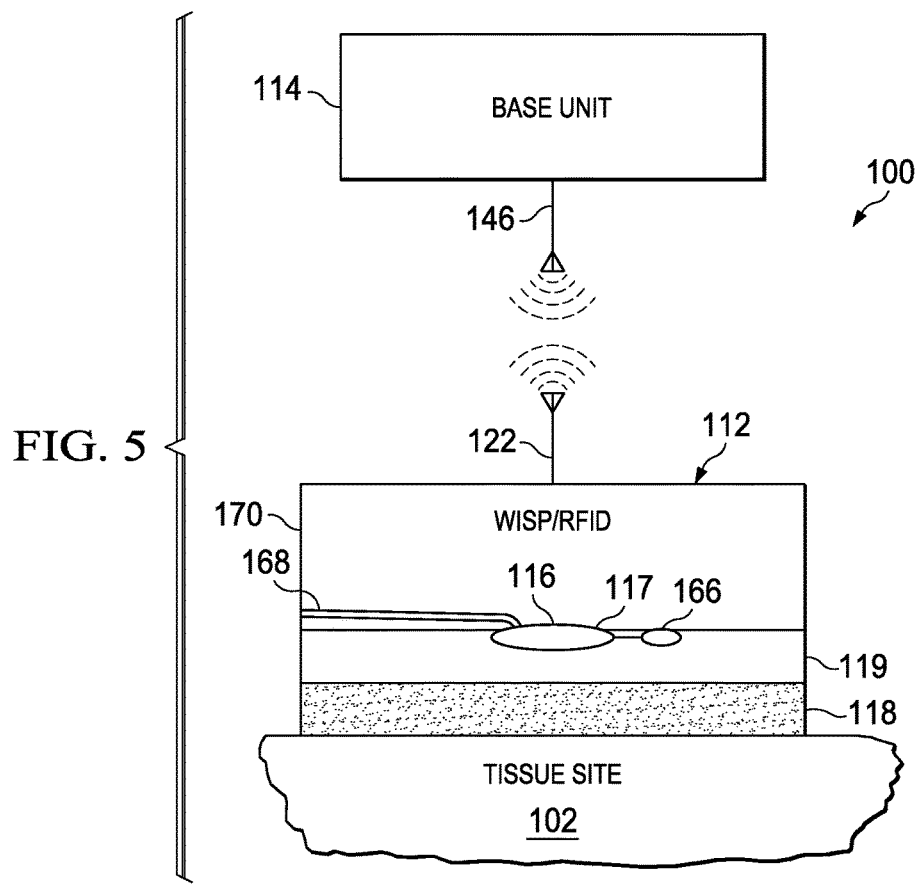
FIG. 5 is a schematic diagram, with a portion shown in cross section, of an illustrative embodiment of a system for treating at least one tissue site with reduced pressure.

Referring now primarily to FIG. 5, another illustrative embodiment of a system 100 for treating at least one tissue site 102 with reduced pressure is presented. The system 100 includes a first, wireless, reduced-pressure dressing 112. The system 100 is similar to the system 100 of FIGS. 1-3, except that a reduced-pressure source 116 is a micro-pump 117, e.g., a piezoelectric pump, and is adjacent to the distribution manifold 118. In addition, an absorbent layer 119 may be included. As used throughout this document in connection with the micro-pump 117, "adjacent" means next to, in the vicinity of, and also includes in.

A dedicated battery 166 may be coupled to the micro-pump 117 to provide power to the micro-pump 117. A vent line 168 may be used to allow the micro-pump 117 to vent or exhaust outside of the first, wireless, reduced-pressure dressing 112. In this embodiment, a first processor (analogous to first processor 124 of FIG. 3) that is associated with a WISP or RFID device 170, may be instructed by the remote base unit 114 to deliver a control signal to the micro-pump 117 when necessary. In another illustrative embodiment, the first processor may receive a pressure message signal indicative of the pressure at the distribution manifold 118, compare the pressure to a target pressure, and in response deliver a control signal to the micro-pump 117 to control the micro-pump 117 as needed. In another illustrative embodiment, the device 170 may harvest power to not only energize the first processor and first sensor, but also the micro-pump 117. A capacitor (not explicitly shown) may be included to help build and retain a charge for powering devices in the first, wireless, reduced-pressure dressing 112.

Referring now to FIGS. 3, 4, and 6, and primarily to FIG. 6, a treatment process that may be executed with the system 100 is presented. The process begins at 200. At step 202, the remote base unit 114 transmits an activation signal to the first, wireless, reduced-pressure dressing 112. The first RFID antenna 122 receives the activation signal. The activation signal energizes the first processor 124. The first processor 124 activates the dissolution element 162. The dissolution element 162 changes the membrane 160 from an occlusive state to a non-occlusive state that allows flow. It should be appreciated that the need to change the membrane 160 to a non-occlusive state helps make sure that only appropriate (approved) remote base units 114 are used with the first, wireless, reduced-pressure dressing 112.

At step 204, the remote base unit 114 transmits an ID inquiry signal to the first, wireless, reduced-pressure dressing 112. The first RFID antenna 122 receives the ID inquiry signal. The ID inquiry signal energizes the first processor 124 and provides an identification request to the first processor 124. In response, the first processor 124 transmits an ID message signal from the first RFID antenna 122 to the RFID reader 146 on the remote base unit 114. The remote base unit 114 waits for the ID message signal at interrogatory 206.

At interrogatory 206, the second processor 148 waits a predetermined time for the ID message signal. If the ID message signal is not received during the predetermined time, the process proceeds to step 208 where an error flag is posted and the process ends at 210. The error flag may include posting a message for display at control panel 158 or sounding an alarm or providing other notification. If the ID message signal is received, the process proceeds to interrogatory 212.

At interrogatory 212, inquiry is made as to whether the ID message signal represents a dressing that is acceptable or approved. To answer the inquiry, the second processor 148 compares the dressing represented by the ID message signal with a list of acceptable or approved dressings. If the dressing represented by the ID message signal is on the list of acceptable or approved dressings, the process continues to step 214 and if not the process proceeds to step 208 and an error flag is posted and the process ends at 210.

At step 214, a first chronograph, T1, is initiated to keep a running cycle time. The process then proceeds to step 216. At step 216, the second processor 148 provides a control signal via coupling 140 to the reduced-pressure source 116 to activate the reduced-pressure source 116. Once the reduced-pressure source 116 is activated, reduced pressure flows to the first, wireless, reduced-pressure dressing 112.

At step 218, the remote base unit 114 transmits a pressure inquiry signal to the first, wireless, reduced-pressure dressing 112. The first RFID antenna 122 receives the pressure inquiry signal. The pressure inquiry signal energizes the first processor 124 and first sensor 126. In response, the first processor 124 transmits a pressure message signal to the remote base unit 114. The RFID reader 146 receives and delivers the pressure message signal to the second processor 148. At interrogatory 220, the second processor 148 then compares the pressure message signal, which indicates the pressure substantially at the distribution manifold 118 or other desired location, with a target pressure. If the pressure message signal indicates a pressure that is greater than the target pressure on an absolute scale, then more reduced pressure is needed and the delivery of reduced pressure continues. The process proceeds to interrogatory 222. On the other hand, if the pressure message signal indicates a pressure that is less than the target pressure on an absolute scale, then the process proceeds to step 224.

At decision step 222, the second processor 148 compares the elapsed time of the first chronograph, T1, with a maximum time, T1max. If the maximum time has been exceeded, the process continues to step 226. At step 226, the second processor 148 posts an error flag and the process ends at 228. The error flag may include sounding an alarm or displaying a message on the control panel 158 or otherwise notifying the user of a problem. If the maximum time has not been exceeded, the process returns to step 218. The loop (218, 220, 222, 218, . . . ) continues until the maximum time is exceeded or a suitable reduced pressure is reached.

Once the pressure is suitable, the process proceeds to step 224 where the second processor 148 initiates a therapy chronograph that keeps an elapsed time, T2, for therapy. Next, at step 230, the second processor 148 initiates a cycle chronograph, T3. The process then proceeds to interrogatory 232, wherein the elapsed therapy time, T2, is compared to a maximum allowed value. If the elapsed therapy time, T2, is greater than the maximum allowed value, then a flag indicating that therapy is complete is given at step 234 and the process ends 250. Otherwise, the process continues to step 236.

At step 236, the remote base unit 114 transmits a pressure inquiry signal to the first, wireless, reduced-pressure dressing 112. The first RFID antenna 122 receives the pressure inquiry signal. The pressure inquiry signal is then delivered to the first processor 124. The pressure inquiry signal energizes the first processor 124 and the first sensor 126. In response, the first processor 124 develops a pressure message signal. The first processor 124 and first RFID antenna 122 transmit the pressure message signal to the remote base unit 114. The pressure message signal is received and delivered to the second processor 148. At interrogatory 238, the pressure at the distribution manifold 118 (or other desired location) as represented by the pressure message signal is compared to a target value on an absolute scale. If the pressure is greater than the target value, reduced pressure needs to be applied (or continued), and the second processor 148 transmits (or continues) a control signal to the reduced-pressure source 116 at step 240. If the pressure is less than the target value, the process pauses at step 242 and continues to monitor pressure by returning to step 230.

At interrogatory 244, the elapsed cycle time, T3, is compared to a maximum value, T3max. If the elapsed cycle time T3 is greater than the maximum value T3max, the system 100 may be unable to adequately lower the pressure. Such a condition may occur because of a leak. Accordingly, an error flag or alarm is initiated at step 246 and the process ends 248. If the elapsed cycle time, T3, is less than the maximum value, T3max, the cycle continues with the process going to interrogatory 232.

Figure 6A:
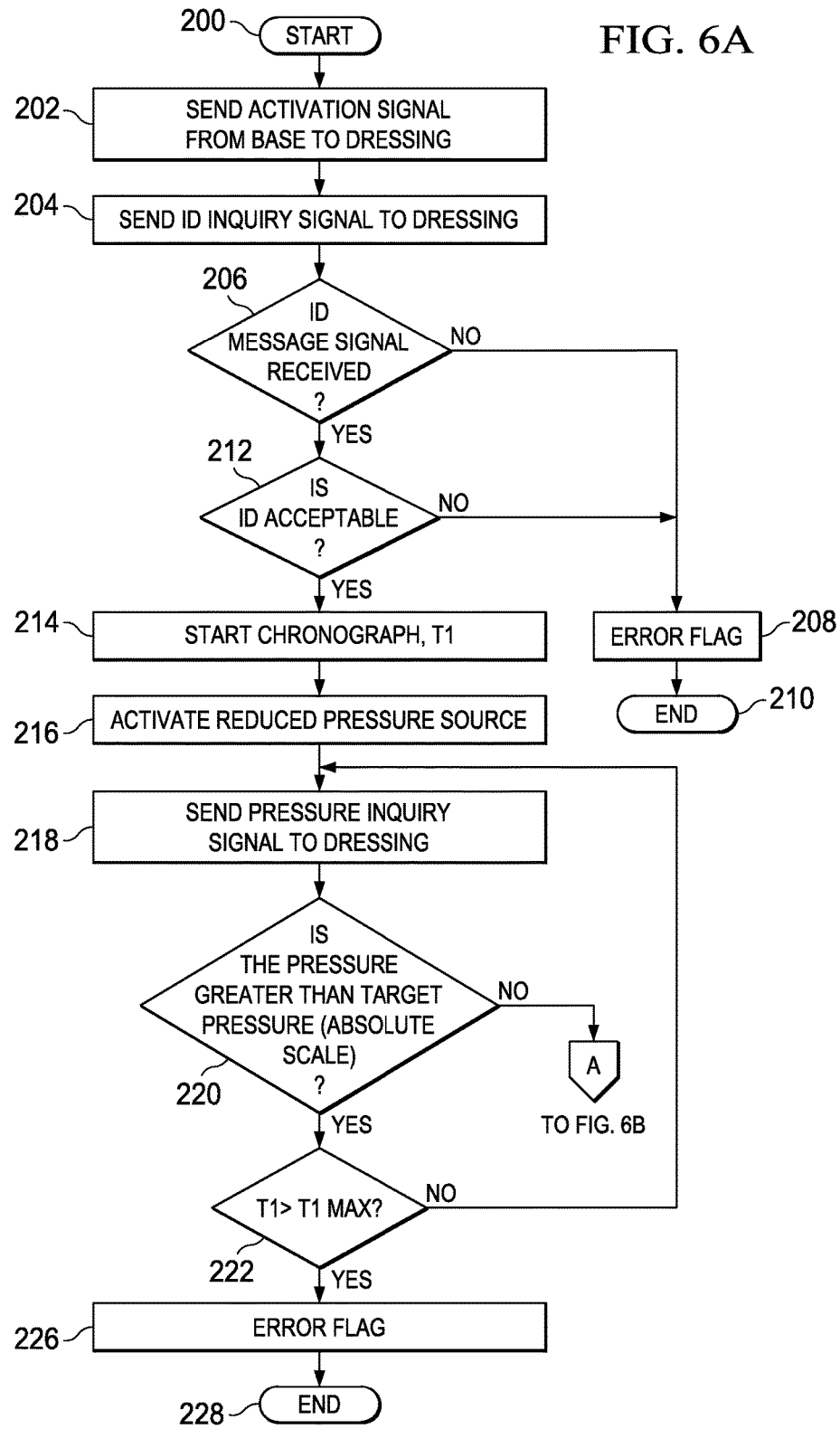
FIGS. 6A and 6B are an illustrative embodiment of a process flow chart for a system for treating at least one tissue site with reduced pressure.
Figure 6B:
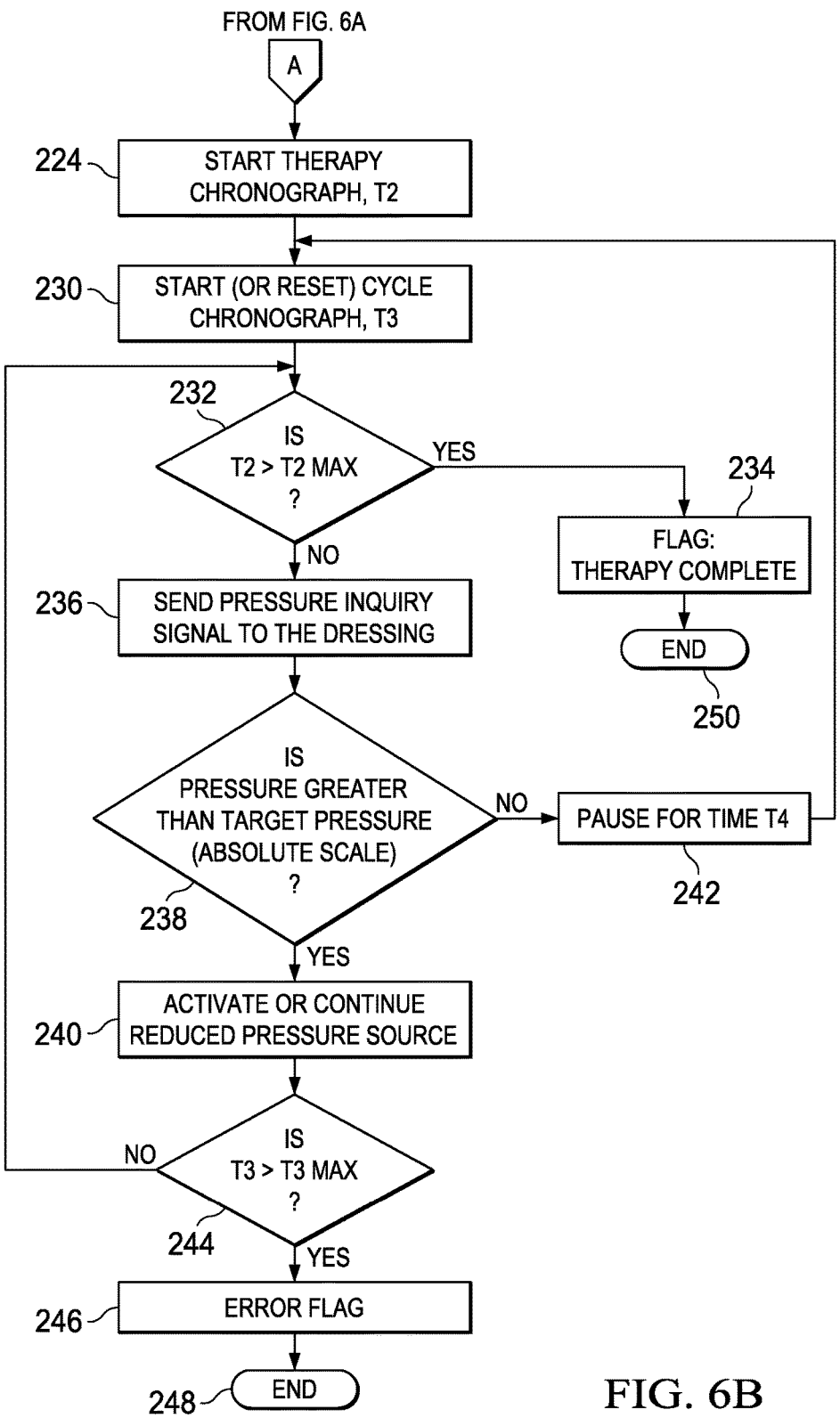

The process presented in FIGS. 6A-6B is one illustrative embodiment. Many embodiments are possible. Other process flows may include analogous instructions for receiving temperature message signals from the second sensor 142 or other data depending on the sensor type. In another illustrative embodiment, the activation step may follow the steps required to confirm an approved dressing.

Since the pressure measurements are taken at the first, wireless, reduced-pressure dressing 112 and wirelessly transmitted to the remote base unit 114, the reduced-pressure delivery conduit 134 may be relatively small as a pressure sensing lumen is not required as part of the reduced-pressure delivery conduit 134. In other words, pressure is measured and the pressure signal is transmitted to the remote base unit 114 without transmission through a wire and without requiring sampling pressure to be communicated through the reduced-pressure delivery conduit 134.

In another illustrative embodiment, the first, wireless, reduced-pressure dressing may be a distribution manifold enclosed by a drape that has been fenestrated or otherwise allows flow. This illustrative embodiment is suitable for use in a body cavity that is closed, such as placing one in an abdominal cavity and monitoring pressure therein. In such an embodiment, the pressure sensor or other sensors may be located anywhere in or on the dressing and are operable to communicate with a remote base outside of the body cavity. In one embodiment, the pressure sensor may be located at peripheral edge of the dressing that is used in an abdominal cavity. The peripheral edge is disposed near the patient's paracolic gutter to monitor pressure and fluid removal.

The RFID antenna and first processor may be adapted to provide an identification message signal for other purposes than those previously presented. For example, in addition to utilization of the identification message signal to confirm proper pairing of a dressing and base, the identification message signal may be used for inventory purposes. A scanner with a RFID reader may be used to scan a wireless, reduced-pressure dressing and receive the identification message signal.

In another illustrative embodiment, a release pouch is provided that contains a fluid. The release pouch may be formed as part of a wireless, reduced-pressure dressing. The release pouch may be formed, for example, by an additional membrane attached on a patient-facing side of the sealing member. A dissolution element analogous to dissolution element 162 may be associated with the release pouch. The dissolution element allows the first processor 124 to selectively dissolve or open a portion of the release pouch to release any contents of the pouch. Thus, the release pouch may be used to retain medicines or other substances and a wireless signal may be sent to the wireless, reduced-pressure dressing causing release of the medicine. For example, if a sensor detects bacterial colonization, a signal may be sent opening the pouch and releasing an anti-biotic, or if high blood content is detected, a signal may be sent releasing a coagulent.

In some embodiments of the wireless, reduced-pressure dressing, the RFID antenna may be remote from the first processor, but electrically coupled to the first processor. For example, a larger RFID antenna may be used on the patient near the tissue site to be treated, and a coupling wire may extend from the RFID antenna to the first processor or first sensor adjacent to or on the distribution manifold.

Although the subject matter of this disclosure has been described in the context of certain illustrative, non-limiting embodiments, various changes, substitutions, permutations, and alterations can be made without departing from the scope of the disclosure as defined by the appended claims. Further, any feature that is described in connection to any one embodiment may also be applicable to any other embodiment. For example, the benefits and advantages described above may relate to one embodiment or may relate to several embodiments. Where appropriate, aspects of any of the embodiments described above may be combined with aspects of any of the other embodiments described to form further examples having comparable or different properties and addressing the same or different problems. Additionally, the steps of the methods described herein may be carried out in any suitable order, or simultaneously where appropriate.

What is claimed is:

1. A system to treat at least one tissue site with reduced pressure, the system comprising:
    a first, wireless, reduced-pressure dressing configured to be disposed proximate to the at least one tissue site, wherein the first, wireless, reduced-pressure dressing comprises:
        a distribution manifold,
        a sealing member covering at least a portion of the distribution manifold,
        a radio-frequency identification (RFID) tag antenna,
        a first processor coupled to the RFID tag antenna,
        a reduced-pressure interface adapted to fluidly couple a reduced-pressure source to the distribution manifold through the sealing member,
        wherein the reduced-pressure source is adapted to be positioned external to the first, wireless, reduced-pressure dressing and to be fluidly coupled to the reduced-pressure interface through a reduced-pressure delivery conduit, and wherein the RFID tag antenna is configured as a coil in at least a portion of a perimeter of the reduced-pressure interface, and
        a first sensor coupled to the first processor, wherein the first sensor is a pressure sensor comprising a strain gauge supported by a deflector, the first sensor having a first side exposed to an ambient atmosphere and a second side exposed to the at least one tissue site, and wherein the first sensor is integrally formed with the reduced-pressure interface; and
    a remote base device comprising an RFID reader and a second processor coupled to the RFID reader, wherein the remote base device further comprises a pressure indicator.

2. The system of claim 1, wherein the first, wireless, reduced-pressure dressing further comprises at least one of a temperature sensor, a pH sensor, a humidity sensor, a volatile organic compound sensor, a blood sensor, or a growth factor sensor.

3. The system of claim 1, wherein the reduced-pressure source is coupled to the remote base device, and wherein the remote base device is configured to supply a pressure control signal to the reduced-pressure source.

4. The system of claim 1, wherein the reduced-pressure source and the remote base device comprise an integrated treatment device.

5. The system of claim 1, wherein the second processor is configured to receive an identification (ID) signal and to determine if the ID signal represents an approved dressing.

6. The system of claim 1, wherein the at least one tissue site comprises a first tissue site and a second tissue site, wherein the first, wireless, reduced-pressure dressing is configured to be positioned adjacent to the first tissue site, and wherein the system further comprises a second, wireless, reduced-pressure dressing that is configured to be positioned adjacent to the second tissue site.

7. The system of claim 1, wherein the strain gauge is a layer of the deflector.

8. The system of claim 1, wherein the strain gauge and the deflector are configured such that a deflection of the deflector imparts a deflection of the strain gauge.

9. The system of claim 8, wherein the strain gauge has an electrical resistance value, and wherein the deflection of the strain gauge corresponds to a change in the electrical resistance value of the strain gauge.

10. The system of claim 8, wherein the strain gauge has an electrical resistance value, and wherein the deflection of the strain gauge is proportional to a change in the electrical resistance value of the strain gauge.

11. The system of claim 1, wherein the RFID tag antenna and the first processor are formed integrally with the reduced pressure interface.

12. The system of claim 1, wherein the RFID tag antenna and the first processor are positioned on the reduced pressure interface.

13. A system to treat at least one tissue site with reduced pressure, the system comprising:

a wireless, reduced-pressure dressing configured to be disposed proximate to the at least one tissue site, wherein the wireless, reduced-pressure dressing comprises:
a sealing member configured to cover at least a portion of the at least one tissue site,
a first processor,
a radio-frequency identification (RFID) tag antenna coupled to the first processor,
a reduced-pressure interface adapted to fluidly couple a reduced-pressure source to the at least one tissue site through the sealing member, wherein the reduced-pressure source is adapted to be positioned external to the wireless, reduced-pressure dressing and to be fluidly coupled to the reduced-pressure interface through a reduced-pressure delivery conduit, and wherein the RFID tag antenna is configured as a coil in at least a portion of a perimeter of the reduced-pressure interface, and
a first sensor coupled to the first processor, wherein the first sensor is a pressure sensor comprising a strain gauge supported by a deflector, wherein the first sensor has a first side exposed to an ambient atmosphere and a second side exposed to the at least one tissue site, and wherein the first sensor is integrally formed with the reduced-pressure interface.

14. The system of claim 13, wherein the strain gauge and the deflector are configured such that a deflection of the deflector imparts a deflection of the strain gauge.

15. The system of claim 13, wherein the strain gauge has an electrical resistance value, and wherein a deflection of the strain gauge corresponds to a change in the electrical resistance value of the strain gauge.

16. The system of claim 13, wherein the strain gauge has an electrical resistance value, and wherein a deflection of the strain gauge is proportional to a change in the electrical resistance value of the strain gauge.

17. The system of claim 13, wherein the RFID tag antenna and the first processor are formed integrally with the reduced pressure interface.

18. The system of claim 13, wherein the RFID tag antenna and the first processor are positioned on the reduced pressure interface.

19. A system to treat at least one tissue site with reduced pressure, the system comprising:
a wireless, reduced-pressure dressing configured to be disposed proximate to the at least one tissue site, wherein the wireless, reduced-pressure dressing comprises:
a sealing member configured to cover at least a portion of the at least one tissue site,
a first processor,
a radio-frequency identification (RFID) tag antenna coupled to the first processor, and
a first sensor coupled to the first processor, wherein the first sensor is a pressure sensor having a first side exposed to an ambient atmosphere and a second side exposed to the at least one tissue site, and wherein the first sensor comprises a strain gauge supported by a deflector;
a reduced-pressure source configured to be positioned external to the wireless, reduced-pressure dressing; and
a reduced-pressure interface configured to fluidly couple the reduced-pressure source to the wireless, reduced-pressure dressing through a reduced-pressure delivery conduit, wherein the RFID tag antenna is configured as a coil in at least a portion of a perimeter of the reduced-pressure interface.

20. The system of claim 19, wherein the strain gauge and the deflector are configured such that a deflection of the deflector imparts a deflection of the strain gauge.

21. The system of claim 19, wherein the strain gauge has an electrical resistance value, and wherein a deflection of the strain gauge corresponds to a change in the electrical resistance value of the strain gauge.

22. The system of claim 19, wherein the strain gauge has an electrical resistance value, and wherein a deflection of the strain gauge is proportional to a change in the electrical resistance value of the strain gauge.

23. The system of claim 19, wherein the RFID tag antenna the first processor are formed integrally with the reduced pressure interface.

24. The system of claim 1, wherein the reduced-pressure source comprises a micro-pump.

* * * * *